United States Patent
Al-Qahtani et al.

(10) Patent No.: US 11,980,591 B1
(45) Date of Patent: May 14, 2024

(54) SMART PHARMACEUTICAL DRUG BOX

(71) Applicant: KING SAUD UNIVERSITY, Riyadh (SA)

(72) Inventors: Mahdi Al-Qahtani, Riyadh (SA); Meteb Altaf, Riyadh (SA); Ravish Javed, Riyadh (SA); Fahad Alluhidan, Riyadh (SA); Rayan Alfuraih, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/207,477

(22) Filed: Jun. 8, 2023

(51) Int. Cl.
  *A61J 1/05* (2006.01)
  *A61J 7/00* (2006.01)
  *A61J 7/04* (2006.01)

(52) U.S. Cl.
  CPC ........... *A61J 7/0454* (2015.05); *A61J 7/0084* (2013.01); *A61J 7/0427* (2015.05); *A61J 1/05* (2013.01)

(58) Field of Classification Search
  CPC .................................................. A61J 7/0427
  See application file for complete search history.

(56) References Cited

U.S. PATENT DOCUMENTS

| | | | |
|---|---|---|---|
| 3,917,045 A * | 11/1975 | Williams | G07F 9/002 221/15 |
| 6,848,593 B2 | 2/2005 | Papp | |
| 7,359,765 B2 | 4/2008 | Varvarelis et al. | |
| 7,885,725 B2 * | 2/2011 | Dunn | G07F 9/02 700/244 |
| 9,760,691 B2 | 9/2017 | Seeger | |
| 10,304,562 B2 | 5/2019 | Turnell et al. | |
| 2003/0036683 A1 | 2/2003 | Kehr et al. | |
| 2009/0037217 A1 * | 2/2009 | Naik | A61J 7/04 705/2 |
| 2010/0185456 A1 | 7/2010 | Kansal | |
| 2014/0309769 A1 * | 10/2014 | Wu | A61J 7/0084 700/232 |
| 2018/0308571 A1 | 10/2018 | Tupler et al. | |

FOREIGN PATENT DOCUMENTS

IN 201931029876 A 8/2019

OTHER PUBLICATIONS

"Hero automatic pill dispenser," © Hero Health, Inc. 2020.
"Philips Medication Dispenser," © 2004-2020 Koninklijke Philips N.V.
"MedaCube".

* cited by examiner

*Primary Examiner* — Gene O Crawford
*Assistant Examiner* — Ayodeji T Ojofeitimi
(74) *Attorney, Agent, or Firm* — Nath, Goldberg & Meyer; Richard C. Litman

(57) ABSTRACT

A medication dispensing device that includes a medication holding container for holding medication to be dispensed; a dispensing mechanism in communication with the medication holding container configured for dispensing medication from the medication holding container; a communication module in communication with the dispensing mechanism that activates the dispensing mechanism to dispense medication from the medication holding container after receiving a signal from a control device; and a synchronization module that keeps track of signals sent from the control device to the medication dispensing device.

5 Claims, 5 Drawing Sheets

SMART PHARMACEUTICAL DRUG BOX

BACKGROUND

1. Field

This disclosure relates to devices such as a smart pharmaceutical drug box used to dispense medication.

2. Description of the Related Art

Regularity in taking medication can be challenging for many people, especially the elderly. Elderly people and even younger people can forget to take the proper medication at the prescribed time with appropriate dosages. Forgetting to take a medication or taking too much of a medication can have dangerous consequences in some cases. In order to expedite the recovery process, a patient must take appropriate medication in an appropriate quantity and at the appropriate time.

SUMMARY

A smart pharmaceutical drug box can store and dispense medicine to patients in a timely and efficient manner. A GUI on a smart phone can be connected to the smart pharmaceutical drug box wirelessly. The smart pharmaceutical drug box is configured to sense temperature in the drug box and notify the user to take medicine stored in the drug box. If the temperature of the smart pharmaceutical drug box is not maintained within a set range, an alert is given to adjust the temperature.

The smart pharmaceutical drug box in one embodiment is a medication dispensing device that includes: a medication holding container that holds medication to be dispensed; a dispensing mechanism in communication with the medication holding container that is configured to dispense medication from the medication holding container; and a communication module in communication with the dispensing mechanism that activates the dispensing mechanism to dispense medication from the medication holding container after receiving a signal from a control device.

A medication dispensing system many include more than one medication dispensing devices and a synchronization module that keeps track of signals sent from the control device to each medication dispensing device so that a patient may use more than one medication dispensing device to dispense the patient's medication. For instance, a patient may have one medication dispensing device at home and another at work. The synchronization module keeps track of medication being taken from both home and work, giving that patient more flexibility.

In another embodiment a medication dispensing device includes: a medication holding container that holds medication to be dispensed; a dispensing mechanism in communication with the medication holding container that is configured for dispensing medication from the medication holding container; a communication module in communication with the dispending mechanism; and a control device that, when prompted, sends a signal to the communication module to activate the dispensing mechanism to dispense medication from the medication holding container.

The control device, when prompted, communicates with a synchronization module which keeps track of signals sent to each medication dispensing device in a medication dispensing system so that a patient may use more than one medication dispensing device to dispense the patient's medication.

In a further embodiment, instructions to dispense medication are stored in a non-transitory computer readable medium. The instructions to dispense medication include: sending a signal from a control device to a communication module of a medication dispensing device to activate a dispensing mechanism in communicate with the communication module to dispense medication from a medication holding container in communication with the dispensing device; and recording information on the medication dispensed from the medication holding container.

The instructions can further include: sending an activation signal through a control device to a communication module of an alternate medication dispensing device to activate a dispensing mechanism in communication with the communication module to dispense medication from a medication holding container in communication with the dispensing device; and synchronizing information on medication dispensed from the alternate medication holding container with medication dispensed from the medication holding container so that a patient may use more than one medication dispensing device to dispense the patient's medication.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A medication dispensing device, according to the present teachings, can store and dispense medical tablets and liquid/syrup medicine to patients. The quantities of medication can be released as prescribed by a doctor. The prescription can be stored in hardware by using a GUI on a smart phone which is wirelessly connected to a smart pharmaceutical drug box. The GUI can be used by every age group. The smart pharmaceutical drug box is configured to sense the temperature in the drug box. If the temperature of the smart pharmaceutical drug box is not maintained within a set range, an alert is given so that the temperature can be adjusted. Keeping the temperature within a certain range keeps the chemical properties of the medication from being altered and ensures no loss of potency.

Figure 1:
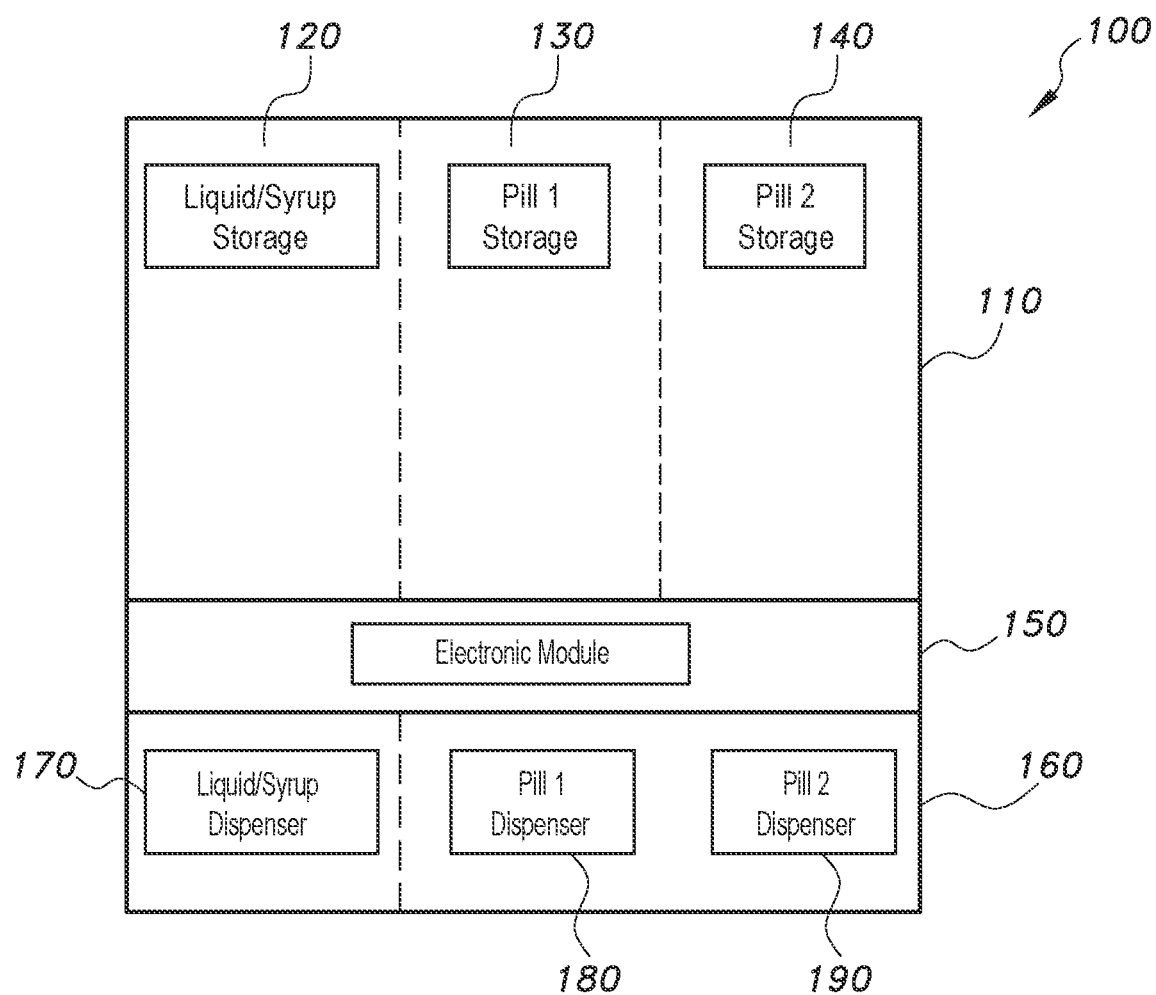
FIG. 1 is an illustration of a smart pharmaceutical drug box.

FIG. 1 is an illustration of a smart pharmaceutical drug box. The illustration depicts a medication dispensing device 100 that includes a medication holding container 110. The medication holding container 110, as illustrated, includes a liquid/syrup/powder storage 120, a first pill storage 130, and a second pill storage 140.

In this embodiment, the medication dispensing device is capable of dispensing three types of medication to a patient. A liquid, syrup or powder medication can be dispensed from the liquid/syrup/powder storage 120 and a first pill type and a second pill type can be dispensed from a first pill storage 130 and second pill storage 140, respectively.

An electronic module 150 (communication module) is connected to the liquid/syrup/powder storage 120, the first pill storage 130 and the second pill storage 140, and operates to dispense medication from each of the liquid/syrup/powder storage 120, the first pill storage 130 and the second pill storage 140.

The electronic module 150 is programmed to dispense medication in accordance with a doctor's prescription and keeps track of when medication should be taken and when medication has been taken. Alerts can also be programmed into the electronic module 150 to alert a patient to take medication or alert a user that medication in medication holding container 110 needs to be refilled.

Medication may not always need to be dispensed at the same time. Medication stored in first pill storage 130 and second pill storage 140 may be dispensed at different times. Likewise, medication stored in liquid/syrup/powder storage 120 may be dispensed at a different time and in different amounts in accordance with a doctor's prescription.

Once the electronic module 150 has dispensed medication from the medication holding container 110, the medication is transferred to a dispensed medication container 160.

Medication dispensed from the liquid/syrup/powder storage 120 is dispensed into a dispensed liquid/syrup/powder container 170 located under the liquid/syrup/powder storage 120, and medication dispensed from the first pill storage 130 and second pill storage 140 are dispensed into first pill container 180 and second pill container 190 located under the first pill storage 130 and second pill storage 140, respectively.

Figure 2:
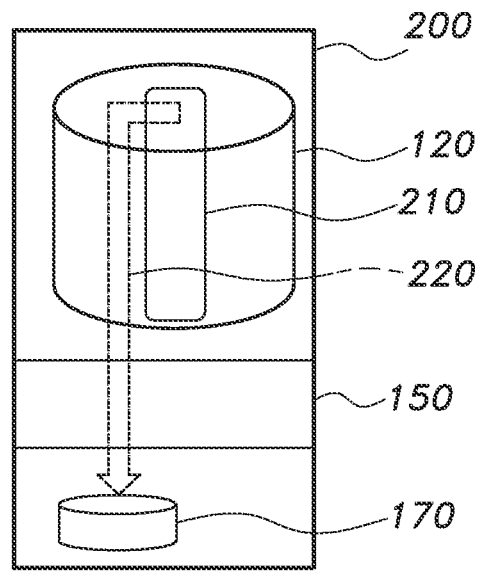
FIG. 2 is an illustration of a liquid/syrup/powder medication dispensing mechanism.

FIG. 2 is an illustration of a liquid/syrup/powder medication dispensing mechanism 200 including the liquid/syrup/powder storage 120 which is used to store liquid medication, a syrup medication or a powder medication. A pump 210 is located within the liquid/syrup/powder storage 120 and is used to dispense medication stored in the liquid/syrup/powder storage 120. A liquid/syrup/powder medication channel 220 extends from the pump to the dispensed liquid/syrup/powder container 170. When the electronic module 150 activates the pump 210, medication contained in the liquid/syrup/powder storage 120 is pumped through the liquid/syrup/powder channel 220 to the dispensed liquid/syrup/powder container 170. A patient can then take the medication pumped into the dispensed liquid/syrup/powder container 170.

Figure 3:
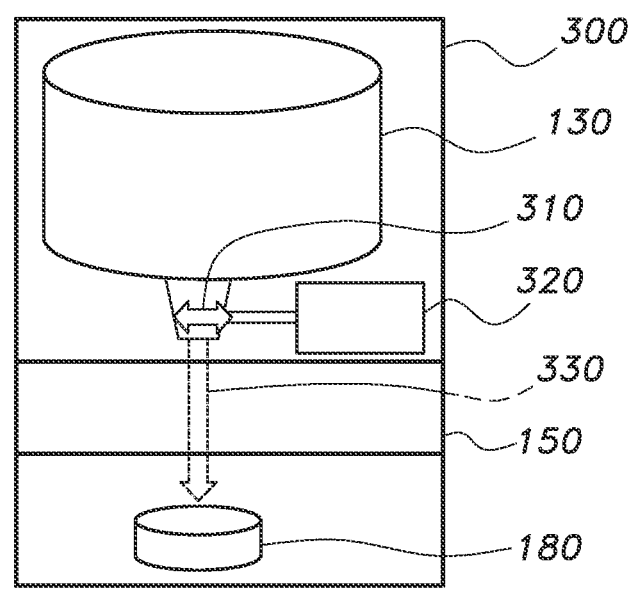
FIG. 3 is an illustration of a pill medication dispensing mechanism.

FIG. 3 is an illustration of a pill medication dispensing mechanism 300. Pills are stored in first pill storage 130. An adjustable lever 310 is located at a bottom portion of the first pill storage 130 and is movable between an open state and closed state. A motor 320 operates to move the adjustable lever 310 when receiving an activate signal from the electronic module 150. A pill medication channel 330 extends from the adjustable lever 310 to first pill container 180. Once motor 320 is activated by the electronic module 150 to move adjustable lever 310 into an open state, medication stored in first pill storage 130 is transferred to first pill container 180 via the pill medication channel 330. A patient can then take the medication transferred to first pill container 180. The foregoing is a description with respect to first pill storage 130. It should be understood that the second pill storage 140 can be operated in the same manner.

Figure 4:
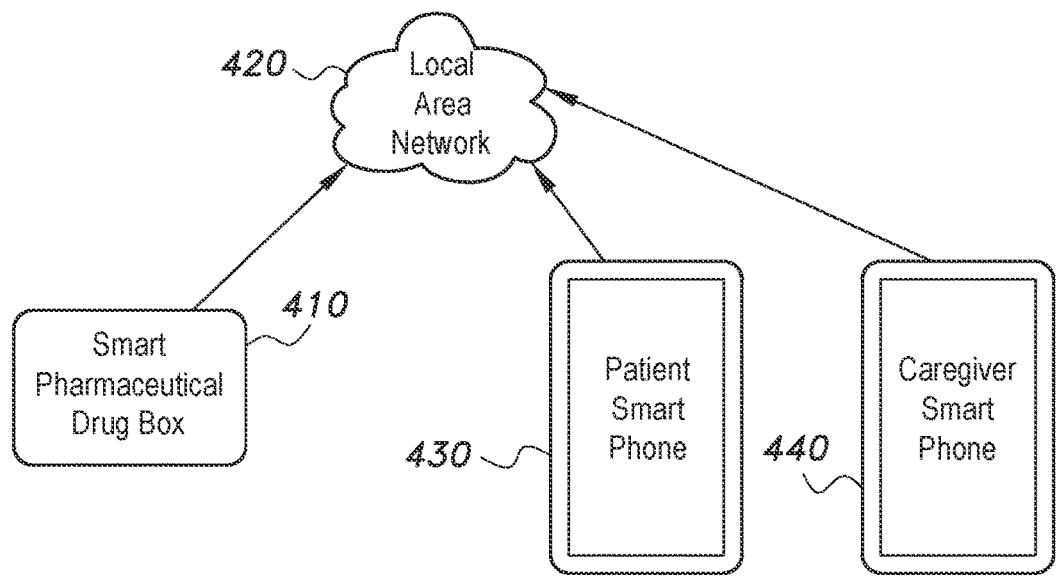
FIG. 4 is an illustration of a smart pharmaceutical drug box that is networked to a local area network.

FIG. 4 is an illustration of a smart pharmaceutical drug box 410 that is networked to a local area network 420. The smart pharmaceutical drug box 410 receives information from a patient smart phone 430 and a caregiver smartphone 440 through the local area network 420. Although smart phones are depicted in FIG. 4 it is understood that other devices may be used that are known in the art.

The smart phones (430,440) can be programed with functions to dispense proper doses of medication at appropriate times as prescribed by a physician, provide an alert that medication should be taken, provide an alert that medication was not taken, provide an alert indicating that a refill of medication is necessary, provide an alert indicating that the temperature has fallen outside a predetermined range, and/or adjust the temperature to fall within a predetermined range. Other functions can include providing instructions for changing a prescription, keeping track of doses of medicine that have been taken and/or need to be taken. The smartphones (430,440) communicate with the smart pharmaceutical drug box 410 through local area network 420 to execute these functions.

Figure 5:
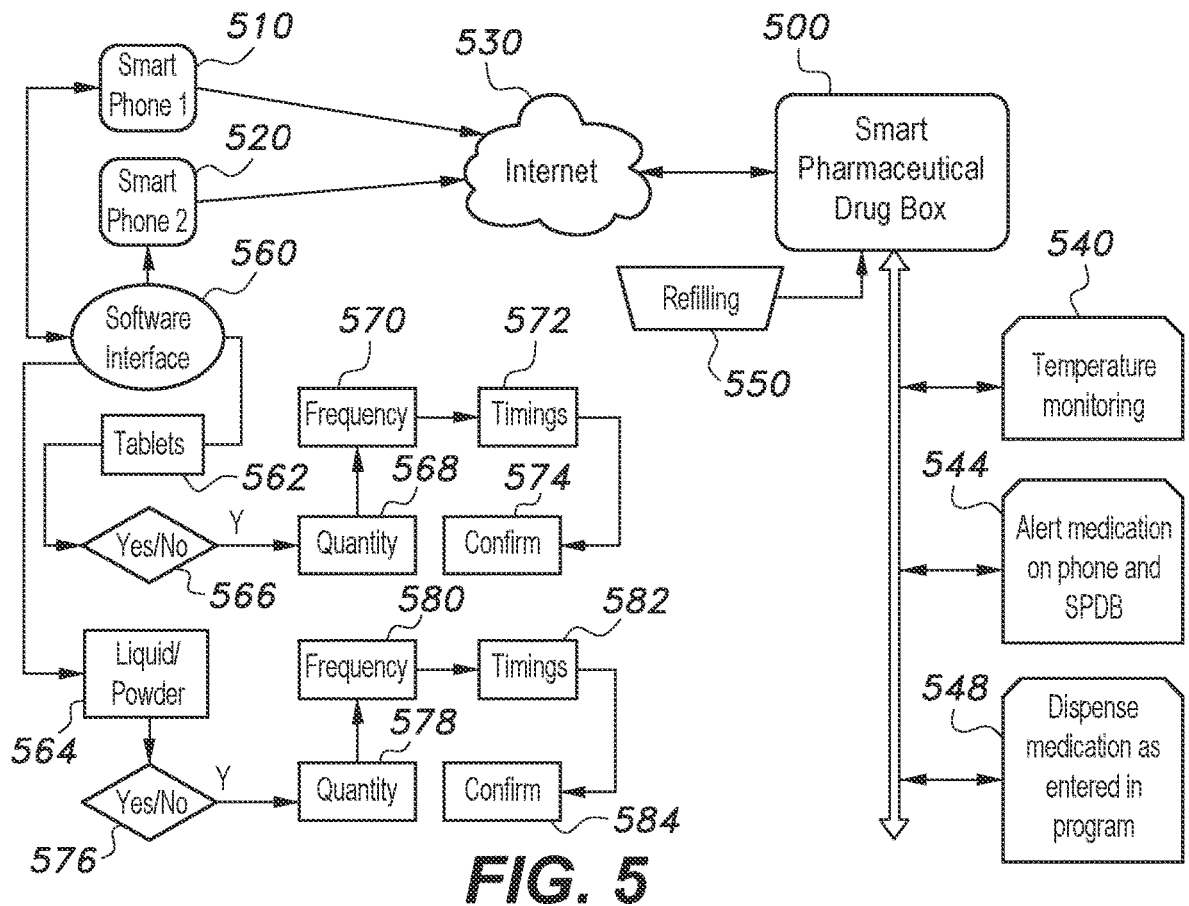
FIG. 5 is a block diagram of the operation of smart pharmaceutical drug box with two smart phones through the Internet.

FIG. 5 is a block diagram depicting the operation of the smart pharmaceutical drug box with smart phone 1 and 2 (510, 520) through Internet 530. Examples of some functions included in smart pharmaceutical drug box 500 are temperature monitoring 540, alert for taking medication 544, and alert for dispensing medication 548.

The temperature monitoring function 540 ensures that the temperature of the smart pharmaceutical drug box 500 is within a predetermined range. If the temperature falls outside the predetermined range, the temperature can be automatically adjusted or an alert can be sent to the smart phones (510, 520) depending on the situation and user preferences.

The alert for medication function 544 sends an alert to at least one of the smart phones (510, 520) and/or the smart pharmaceutical drug box 500 depending on the situation and user preferences. For example, it may be desirable to send an alert to only the patient on smart phone 2 to take the stored medication. In other instances, it may be preferable to send an alert to both smart phones (510, 520) to ensure that the patient takes the stored medicine. This may be helpful in instances when the patient is reluctant to take medication or when the patient needs extra reminders.

The dispense medication function 548 dispenses medication from the smart pharmaceutical drug box 500 at the appropriate times. This can be accomplished by programming the smart pharmaceutical drug box 500 directly or remotely from either of the smart phones (510, 520) through the Internet 530. It is also conceivable that a user could push a button on the smart pharmaceutical drug box 500 to dispense medication and this would be recorded on the smart pharmaceutical drug box 500 or through the Internet 530 to other devices.

Smart phones (510, 520) can be used to keep track of data through a software interface 560. Tablets are tracked in step 562 and liquid/syrup/powder medications are tracked in step 564. In step 566 there is a check to see if there are enough tablets to be dispensed. If there are not enough tablets to be dispensed in step 566 the refilling function 550 is executed. This function could be in the form of an alert sent to smart phones (510, 520) and/or smart pharmaceutical drug box

500. In an embodiment, an alert can be sent to a pharmacy to reorder prescribed medications. In step 568, the quantity of medication is checked. In this step both the quantity of medication left in the smart pharmaceutical drug box is calculated and the quantity of medication that needs to be taken is determined. In step 570, the frequency is updated and checked to ensure that there is not an overdose or under dose of medication. In step 572 the time of day is checked to determine the appropriate time to dispense medication. In step 574, once medication is dispensed, the dispensing of medication is confirmed and recorded.

Liquid/syrup/powder medication is tracked in step 564. In step 576 there is a check to see if there is enough liquid/syrup/powder medication to be dispensed. If there is not enough medication to be dispensed in step 566, the refilling function 550 is executed. This function can be in the form of an alert sent to smart phones (510, 520) and/or smart pharmaceutical drug box 500. It is conceivable that an alert can be sent to a pharmacy to reorder prescribed medications. In step 578 the quantity of medication is checked. In this step both the quantity of medication left in the smart pharmaceutical drug box 500 is calculated and the quantity of medication that needs to be taken is determined. In step 580 the frequency is updated and checked to ensure that there is not an overdose or under dose of medication. In step 582 the time of day is checked to determine the appropriate time to dispense medication. In step 584 the dispensing of medication is confirmed and recorded.

It is notable that in some cases a smart phone, such as smart phone-2 520, may only receive information from software interface 560 (see unidirectional arrow from software interface 560 to smart phone-2 520 in FIG. 5). In these cases, the user of smartphone-2 520 would not have the ability to change the quantity, frequency and timing of the medication, but could only receive alerts and updates on when the medication should be taken. Of course, any updates on when and if medication is being taken could still be recorded. This may safeguard a prescription to be modified only by a caregiver or physician and not a patient.

Figure 6:
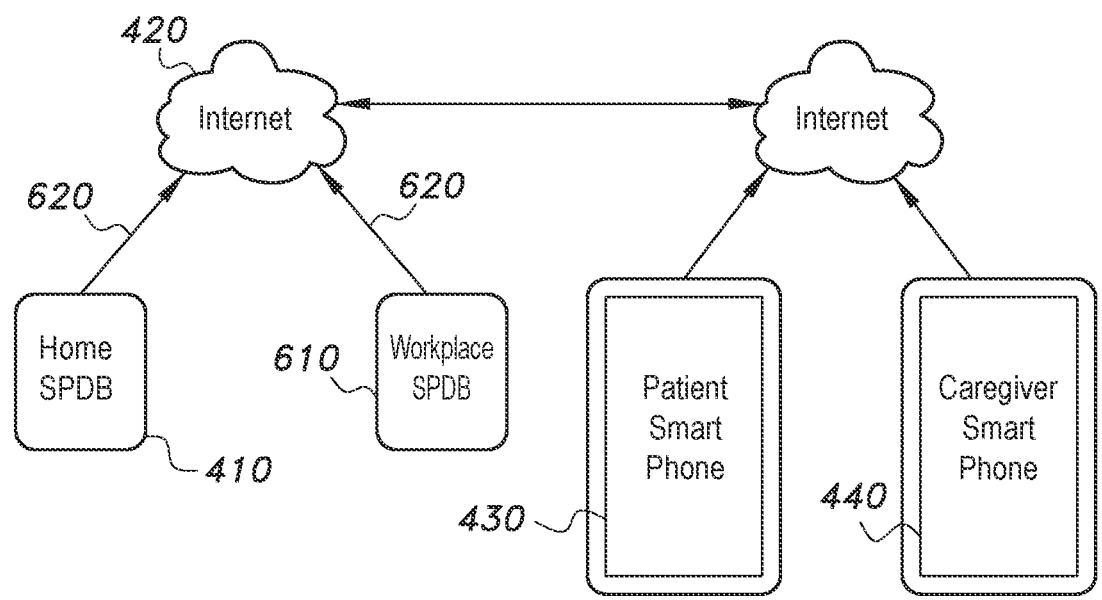
FIG. 6 is an illustration of the use of two smart pharmaceutical drug boxes, one located at home and one located at work.

FIG. 6 is an illustration of the use of two smart pharmaceutical drug boxes. In this example smart pharmaceutical drug box 410 is located at home and smart pharmaceutical drug box 610 is located at work. The operation of smart pharmaceutical drug boxes (410, 610) are the same as discussed in relation to FIG. 4 with the addition of synchronization between smart pharmaceutical drug box 410 and smart pharmaceutical drug box 610. Synchronization 620 (synchronization module) can be in the form of software, hardware or the combination of both in order to keep track of medication being dispensed from each of smart pharmaceutical drug box 410 and 610. For example, if a patient wanted to have the freedom to take medication at home and work, smart pharmaceutical drug box 410 would be used at home and smart pharmaceutical drug box 610 would be used at work. When the patient takes medication at work using smart pharmaceutical drug box 610 this information is recorded and shared with smart pharmaceutical drug box 410 using synchronization 620. Likewise, when the patient takes medication at home using smart pharmaceutical drug box 410, this information is shared with smart pharmaceutical drug box 610 using synchronization 620. If the patient forgets that their medication was taken at work using smart pharmaceutical drug box 610 and tries to take medication at home, smart pharmaceutical drug box 410 would not dispense medication because it will have information using synchronization 620 that the patient already took medication at work. This will prevent overdosing on medication.

Figure 7:
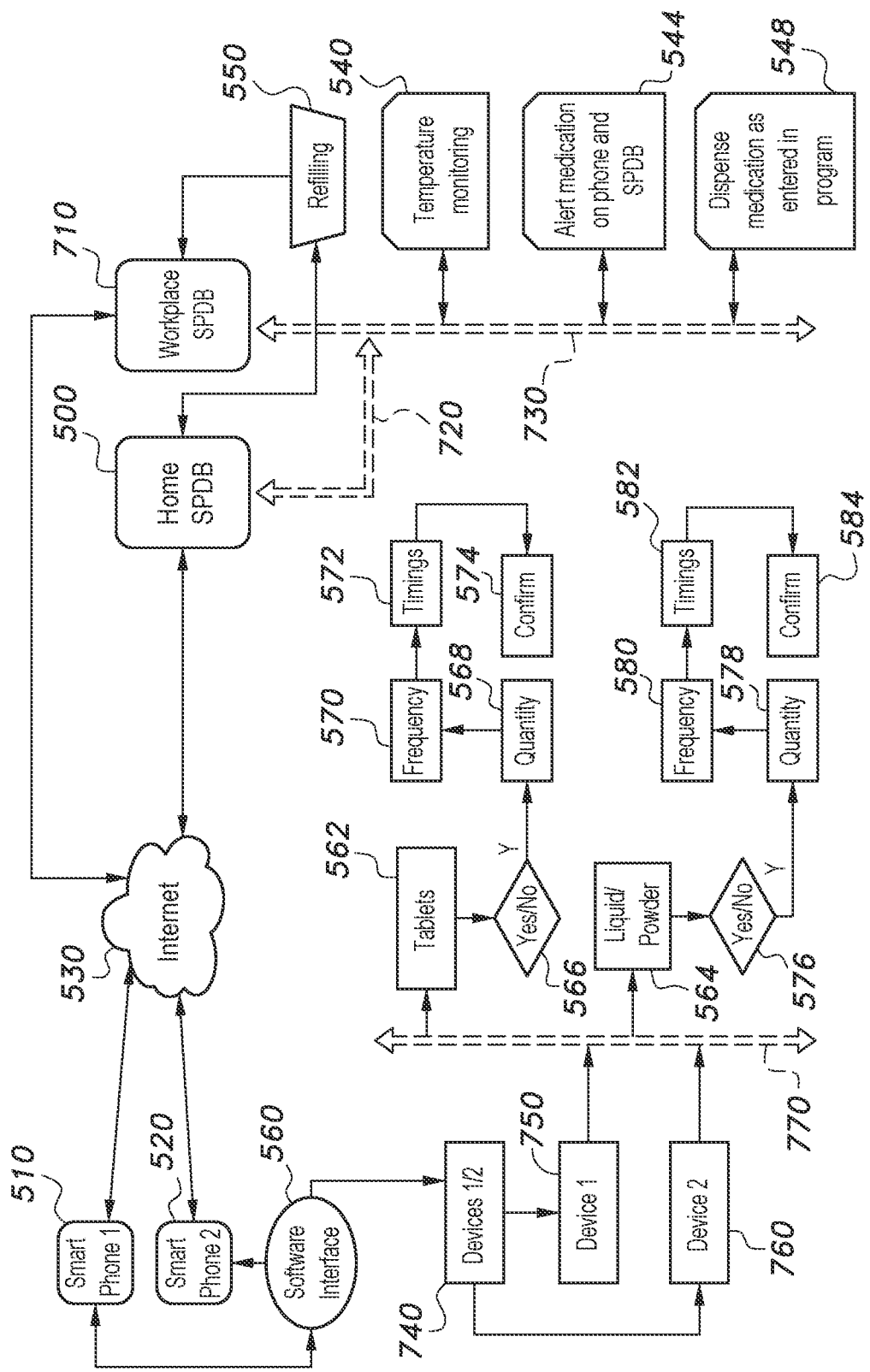
FIG. 7 is an illustration of the operation of two smart pharmaceutical drug boxes to dispense medication.

FIG. 7 is an illustration of the operation of two smart pharmaceutical drug boxes to dispense medication. Smart pharmaceutical drug box 500 operates in the same manner as described in relation to FIG. 5 with the exception of using a work smart pharmaceutical drug box 710 and synchronization 720,730,770. Synchronization 720,730,770 (synchronization module) can be in the form of software, hardware or a combination of both in order keep track of medication being dispensed from each of smart pharmaceutical drug boxes 500 and 710. For example, smart pharmaceutical drug box 500 can be used at home and smart pharmaceutical drug box 710 can be used at work. When the patient takes medication at work using smart pharmaceutical drug box 710, this information can be recorded and shared with smart pharmaceutical drug box 500 using synchronization 720, 730,770. Likewise, when the patient takes medication at home using smart pharmaceutical drug box 500, this information can be shared with smart pharmaceutical drug box 710 using synchronization 720,730,770. If the patient forgets that medication was taken at work using smart pharmaceutical drug box 710 and tries to take medication at home using smart pharmaceutical drug box 500, smart pharmaceutical drug box 500 would not dispense medication because it will have information using synchronization 720,730,770 that the patient already took medication at work. This will prevent overdosing on medication. Synchronization 770 allows for sharing of information such as type of medication taken (562,564), amount of medication available (566, 576), quantity of medication to be taken (568, 578), frequency of taking medication (570,580), timing of taking medication (572,582), and confirmation that medication was dispensed and/or taken (574,584). Synchronization 720, 730 allows for sharing of information between smart pharmaceutical drug box 500 and smart pharmaceutical drug box 710 such as temperature 540, alerts for taking medication 544, dispensing of medication 548, and refilling 550, as discussed in relation to FIG. 5.

The synchronization described herein allows for multiple smart pharmaceutical drug boxes placed in different locations to act as a single unit that dispenses and keeps track of medication that has been dispensed giving users more freedom and ease of use. This will assist in preventing an overdose or overdose of medication and facilitate adhering to prescribed doses of medication according to a doctor's prescription.

In experiment, an embodiment of a smart pharmaceutical drug box was prepared including three levels. The top level included the medication containers, one or more servo motors and a pump. The middle level included electrical components, e.g., Arduino ESP8266 Wi-Fi µC, wires, a temperature sensor, a transistor, a voltage regulator, a buzzer and one or more LEDs. The bottom level included a pill tray for receiving the pills and liquid dispensed from the top level through tubes extending between the pill tray and the top level. The servo motors were configured to release one or more pills from the pill container onto the pill tray. The pump was configured for dispensing liquid medication stored in the drug box. An alarm or buzzer was provided to alert the user that the medication is ready to be taken. In addition, LEDs were provided as indicators to provide helpful information to the user. For example, an LED emitted a first color, e.g., blue, when the pill was ready, a second color, e.g., green, when the liquid medication was ready, and a third color, e.g., red, when the device was connected to an external power source. In experiment, this embodiment of the smart pharmaceutical drug box was prepared as a prototype and all components were connected to a breadboard to program an Arduino ESP8266 Wi-Fi μC; then all the components were soldered together.

For software programing of the prototype, Arduino Integrated Development "Arduino IDE", was used and for the application, BLYNK was used. Arduino IDE contains a text editor for writing the code, a message area, and a text console with a toolbar with buttons for common functions and a series of menus. Arduino IDE connects to the Arduino hardware to upload programs and communicate with them by special libraries. BLYNK is a Platform with iOS and Android apps to control Arduino. It is a digital dashboard for building a graphic interface by just dragging and dropping widgets. In the Arduino IDE, Arduino ESP8266 Wi-Fi μC was programmed to rotate the servo to the desired degree, and calculate the time for the pump to start and stop depending on the desired output, all of which can be modified from the BLYNK application. From the IDE, the buzzer was programmed to start after the pill or the liquid was dispensed; the LEDs were programmed to be activated when the pill and/or liquid was administered; a blue LED was used for administration of the pill; and green LED was used for administration of the liquid.

The box was designed using SOLIDWORKS and the design was printed with a 3*d* printer. SOLIDWORKS software is a mechanical designing application that designers use to sketch out ideas. The design was divided into three sections. The top part of the design was for the medication, the servo motor, and the pump. The middle part was for the electrical components, Arduino ESP8266 Wi-Fi μC and the wires and temperature sensor, transistor, voltage regulator, buzzer and LEDs. The bottom section was for the pill tray for receiving the pills and liquid from the top part through the tubes.

The smart pharmaceutical drug box can improve communication among care providers and patients, and thereby, improve the general comfort and peace of mind of patients. Doctors and caregivers can ensure timely consumption of medication and track medication usage through a secure network interface.

The smart pharmaceutical drug box has a temperature sensor which alerts the patient and caregiver if the temperature inside the drug box exceeds a normal range (as set by the patient or caregiver) to safely secure and protect the medication from spoiling. Alerts for the patient, caregiver, and doctors are used to ensure patients are taking medications in accordance with the prescription. Persistent reminders can be sent to the patient when medication is to be taken, and alerts can be sent to a caregiver in case the patient missed a dose(s). Alerts can also be sent to the patient, caregiver, and pharmacist (or pharmacy) simultaneously to refill the medications (both pill/liquid) three days before the last dose of medicine. In an embodiment, each pill container can hold roughly 100 medium sized tablets, which can easily be refilled by the patient, caregiver, and pharmacist. Storage capacity can also be customized (increased or decreased) with little moderation. If required, additional pill compartments can also be added to the device as per patient requirement. In an embodiment, the liquid container can hold roughly 145 milliliters of liquid medication which can easily be refilled by the patient, caregiver, and pharmacist. Storage capacity can also be customized (increased or decreased). Each medication can have independent and different dispensing times and/or frequency. The smart pharmaceutical drug box can be used for both short or long term and has a user friendly interface on a smart phone.

The drug box can be made from any suitable material, including for example, natural wheat straw fiber casing (100% BPA free. The smart phone software application (BYLINK) is available and free to use on iOS/Android devices. Any small cup or small container can be used to collect the dispensed medication from the device.

It is to be understood that the smart pharmaceutical drug box is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A medication dispensing device comprising:
   a medication holding container for storing medication to be dispensed, wherein the medication holding container comprises:
   a pill holding compartment; and
   a liquid holding compartment;
   a dispensing mechanism in communication with the medication holding container, the dispensing mechanism configured to dispense medication from the medication holding container;
   a control device; and
   a communication module in communication with the dispensing mechanism, the communication module being configured to activate the dispensing mechanism to dispense medication from the medication holding container upon receiving a signal from the control device,
   wherein the dispensing mechanism comprises:
   a servo motor in communication with the pill holding compartment configured for dispensing medication from the pill holding compartment; and
   a pump in communication with the liquid holding compartment configured for dispensing medication from the liquid holding compartment.

2. The device of claim 1, wherein the communication module comprises:
   a receiving module that receives the signal from the control device to activate the dispensing mechanism to dispense medication.

3. A medication dispensing system comprising:
   two or more medication dispensing devices, each device including
   a medication holding container for storing medication to be dispensed, wherein the medication holding container comprises:
   a pill holding compartment; and
   a liquid holding compartment;
   a dispensing mechanism in communication with the medication holding container, the dispensing mechanism configured for dispensing medication from the medication holding container;
   a control device; and
   a communication module in communication with the dispensing mechanism, the communication module being configured to activate the dispensing mechanism to dispense medication from the medication holding container upon receiving a signal from the control device; and
   a synchronization module configured for keeping track of signals sent from the control device to each medication dispensing device,
   wherein the dispensing mechanism comprises:

a servo motor in communication with the pill holding compartment configured for dispensing medication from the pill holding compartment; and a pump in communication with the liquid holding compartment configured for dispensing medication from the liquid holding compartment.

4. The system of claim 3, wherein the communication module comprises:

a receiving module that receives the signal from the control device, the signal activating the dispensing mechanism to dispense medication.

5. A non-transitory computer-readable medium storing instructions to dispense medication, the instructions to dispense medication comprising:

sending a signal from a control device to a communication module of a medication dispensing device to activate a dispensing mechanism in communicate with the communication module to dispense medication from a medication holding container in communication with the dispensing device, wherein the medication holding container comprises:

a pill holding compartment; and a liquid holding compartment; and recording information on medication dispensed from the medication holding container, wherein the dispensing mechanism comprises:

a servo motor in communication with the pill holding compartment configured for dispensing medication from the pill holding compartment; and a pump in communication with the liquid holding compartment configured for dispensing medication from the liquid holding compartment.

* * * * *